United States Patent [19]

Vargas, III

[11] Patent Number: 6,004,325

[45] Date of Patent: Dec. 21, 1999

[54] BIOMEDICAL CEMENT BONDING ENHANCEMENT TUBE

[76] Inventor: Joseph H. Vargas, III, 3 Albert Cree Dr., Rutland, Vt. 05701

[21] Appl. No.: 09/076,081

[22] Filed: May 11, 1998

[51] Int. Cl.⁶ ................................................ A61B 17/58
[52] U.S. Cl. ................................................ 606/94
[58] Field of Search ................... 606/93, 92, 91, 606/94, 95

[56] References Cited

U.S. PATENT DOCUMENTS

| | | | |
|---|---|---|---|
| 4,338,925 | 7/1982 | Miller | 606/94 |
| 4,466,435 | 8/1984 | Murray | 606/94 |
| 4,625,722 | 12/1986 | Murray | 606/94 |
| 4,627,434 | 12/1986 | Murray | 606/94 |
| 5,151,099 | 9/1992 | Young et al. | 606/92 |

*Primary Examiner*—Michael Buiz
*Assistant Examiner*—Tan-Uyen T. Ho

[57] ABSTRACT

An apparatus for facilitating the filling up of a shaft bored into human femoral bone during hip replacement surgery with gelatinous methyl methacrylate bonding cement for receipt of an artificial hip prosthesis so as to maximally prevent loosening of the prosthesis after hardening of the cement consisting of a hollow cylindrically shaped applicator tube, a top end of a hollow first portion thereof which is characterized by the presence of threading threreabouts and a bottom end of which first portion has affixed to it, a top end of a hollow second portion about a centrally located through hole in a base of the first portion with there being affixed to a bottom end of the second portion a circular shaped flexible tip component.

2 Claims, 6 Drawing Sheets

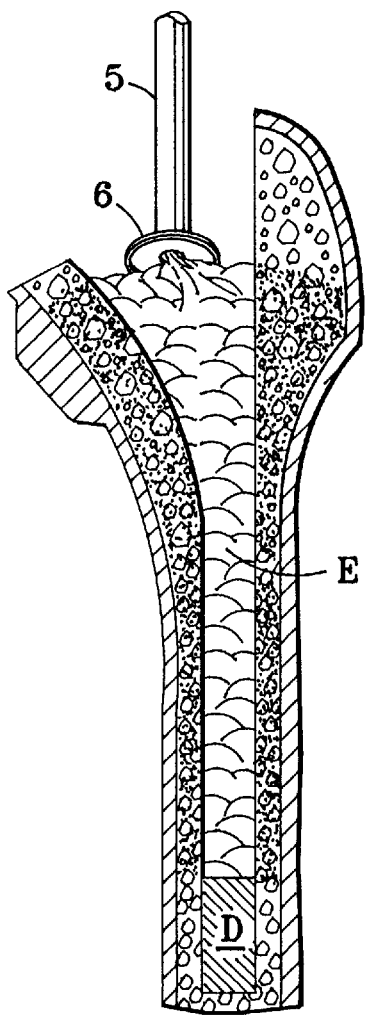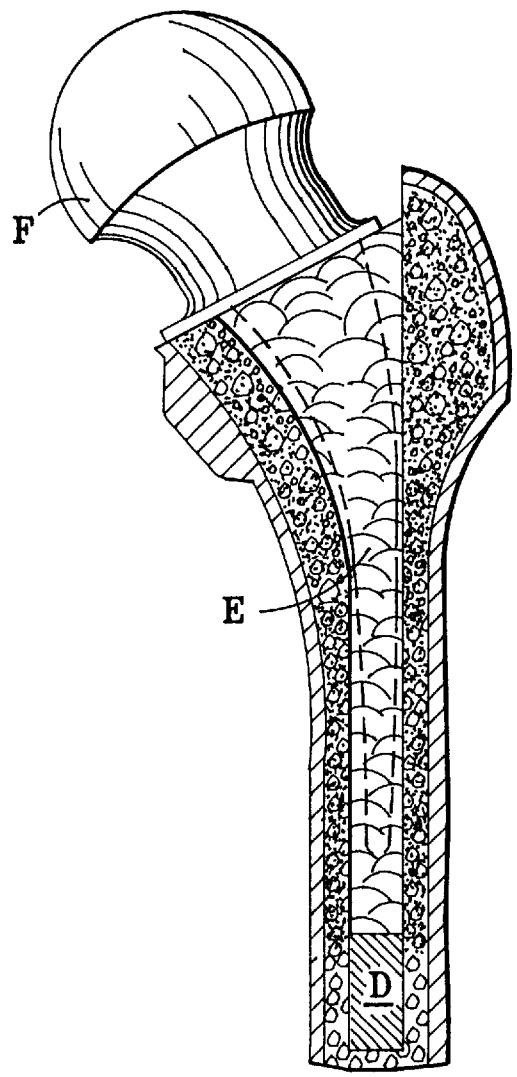
FIG. 16
FIG. 17

BIOMEDICAL CEMENT BONDING ENHANCEMENT TUBE

CROSS REFERENCES TO PRIOR APPLICATIONS

There are no prior parent or related applications in respect of the instant invention.

FEDERALLY SPONSORED RESEARCH AND DEVELOPMENT

There is no federally sponsored research and development in respect of the instant invention.

BACKGROUND OF THE INVENTION

1) Field of the Invention

The instant invention is one of those devices that serves to facilitate the implantation of artificial hip prostheses into the long leg bone of human beings.

Invariably, the primary difficulty with total hip joint replacement procedures as currently performed by orthopaedic surgeons is the tendency of such devices once implanted in human bone to loosen in-situ with the passage of time. For patients who are confronted with such a phenomenon, the choice is simple though unpalatable, namely corrective surgery to be performed in order to alleviate the perambulatory and other problems such as pain and/or discomfort that result from such loosening. It has been demonstrated through studies that there is as much as a 40% loosening rate with respect to such devices per roughly ten year terms of implantation. For reasons that will soon be articulated in more detail, the instant invention serves to markedly militate against such loosening thereby alleviating the eventual need on the part of such patients for such corrective surgery.

Currently, when artificial hip prostheses are implanted into the femoral bones of patients, methyl methacrylate is utilized as a bonding agent in order to bond to the prostheses and at the same time to bond to the bone being implanted to thereby hold the prostheses to such bone. The bonding agent functions to accomplish fixation by way of adherence to an implanted prosthesis and by way of penetration of the interstitial cavitations within such bone structure while in a semi-liquid or gelatinous state such that when it hardens or cures, there is then a basis for such prosthesis fixation to such bone. Briefly stated, the femoral head and top portion of a patient's' femoral bone are surgically excised away from the bone. Then a canal or shaft is bored into the bone, then the canal or shaft is filled with gelatinous methyl methacrylate, then a hip prosthesis with an artificial femoral head of its own is pressed down into the cement filled canal or shaft and found to be relatively firmly in place once said cement hardens. The cement itself is delivered into the shaft under pressure by way of syringe-like gun screwed at its base into a rigid hollow applicator tube. Once the shaft is filled with cement, a spongy tarp is placed over the filled shaft and pressure is applied down on the tarp by the surgeon in an attempt to pack the cement tightly into the shaft and hopefully ultimately into the many small interstitial cavitations lining the boundaries of the shaft.

The primary problem with respect to such loosening as referred to above lies in the bond of cement to bone by way of such cement eventually weakening with the passage of time. The integrity of such bonding is subject to the inevitability of bone growth dynamics. Bone is a living tissue and hence changes its size and shape over time thus actuating the possibility of loosening at the interstitial cavitations into which such cement would have originally been placed change in respect of size and shape. Certain steps have been incorporated into a generally accepted hip replacement surgical protocol in order to combat such a problem. One such step has been the one whereby such cement in its gelatinous state is centrifuged prior to application in order to berid the cement to the greatest possible extent of air vacuoles within it that themselves operate to compromise to no small extent the integrity of the initial bond of such cement to the bone formed by way of such cement's filling of such interstitial cavitations within such bone upon application as such. Moreover, a restrictor cap is placed at the bottom of the shaft prior to filling the shaft in order to prevent the cement from seeping into distal part of the femur at the base of the shaft. Finally tamping down on the bonding cement, as noted above, with a spongy tarp once the shaft is completely filled is yet another precaution taken to hopefully alleviate potential loosening. However, as will be noted with an eye toward the foregoing, notwithstanding such advances in respect of surgical protocol, as matters currently stand in respect of the art of inserting such prostheses into bone, except as respects the success in such regard enjoyed by your inventor with resort to the utilization of his Biomedical Cement Bonding Enhancer as otherwise taught in U.S. Pat. No. 5,468,245 entitled, A Biomedical Cement Bonding Enhancer, no effort in view of the same is now able to be made to markedly minimize such loosening by way of isolating the injected gelatinous cement from air and an inexorable creation of porosity by such air within such cement that adversely affects bonding at the boundaries of the shaft and indeed even within the cement itself in terms of its relative density, also a factor in respect of such loosening until, at last, at least, the above-mentioned spongy tarp is applied.

The instant applicator tube on the other hand, embodies a markedly revolutionary departure from the foregoing art and for reasons that will now be set forth, is indeed, respectfully submitted, new, unique and unquestionably useful. Once a femoral shaft has been bored and a syringe unit is attached to the instant applicator tub after having been filled with gelatinous cement, the instant applicator tube is then inserted into the shaft to a distance of two centimeters or so above a previously inserted resistor cap. The cement is then introduced into the shaft out of the lower end of the instant applicator tube below the level of the circular tip component portion of the instant applicator tube. Such an undertaking causes such injected cement, previously rendered relatively free of air vacuoles and now exposed to virtually no air, to ooze under pressure laterally, much deeper than would have previously been the case with regards to the protocol previously outlined, into the interstitial cavitations within such bone located at the lateral inner boundary of the shaft. Such deeper oozing actuates the potential for much more dependable bonding upon hardening notwithstanding bone growth dynamics over time. Injection into the closed space within the shaft just below the base of the circular shaped flexible tip component of the instant invention to the extent that such tip causes much greater penetration of the interstitial cavitations and hence much greater bone-cement bonding, due to the great increase in local pressure caused by the creation of such a closed space by and in view of the presence of the tip. Greater intra-cement bonding and concomitantly enhanced density absent the potential for the erstwhile creation of air vacuoles, within the cement itself will, once again, be found as well. This much more effective bonding greatly minimizes to a marked degree any potential propensity for eventual loosening. Withdrawal back another two centimeters in distance is followed by more cement being injected into a new enclosed space between the base of the tip and the top surface of the just previously injected cement, and the process is repeated until at last the shaft is filled as tightly as possible with such now relatively air tight gelatinous cement. The applicator tube is removed from the shaft, the spongy tarp is applied to the top layer of the cement, the prosthesis is then firmly inserted into the cement filled shaft and the cement is left to harden thereby resulting in the very firm positioning of a prosthesis so anchored to bone as to most likely markedly minimize any potential propensity for eventual prosthesis loosening.

The means by which the instant device functions so effectively in respect of the foregoing lies in the fact that the circular shaped flexible tip component of the instant applicator tube upon insertion of the tube affixed to the end of a syringe creates a tightly closed shaft space into which cement can be introduced. The tip at its edging adheres firmly to the walling of the shaft thereby creating a succession of airtight subspaces all the while the cement is being injected after successive withdrawals up the shaft. The advantage of the instant invention over the above-mentioned Biomedical Cement Bonding Enhancer, lies in its relative simplicity and concomitantly lower cost of manufacture.

2) Prior Art

Your inventor is not aware of any prior art that anticipates the claims contemplated by the instant invention.

SUMMARY OF THE INVENTION

1. A Brief Description of the Invention

The instant invention consists of a specially modified applicator tube for purposes of introducing methyl methacrylate into a bored femoral shaft in contemplation of the introduction therein of an artificial hip prosthesis. The tube is hollow and cylindrically shaped. A first portion thereof is hollow and cylindrically shaped. Affixed to the base of this first portion, the base being characterized by a hole therein centrally located, is a hollow, cylindrically shaped second portion which has a diameter markedly less than the diameter of the first portion. One embodiment of the instant invention is characterized by threading about the outer walling of the first portion near the upper end thereof. A second embodiment of the instant invention is characterized by threading about the inner walling of the first portion near the upper end thereof. One embodiment permits affixation of the tube to a methyl methacrylate holding syringe with threading about the inner walling near a lower end thereof. The second embodiment permits affixation of the tube to a methyl methacrylate holding syringe unit with threading about the outer walling near a lower end thereof. Both embodiments are characterized by the presence of a circular shaped flexible tip component affixed to the second portion of the tube about the open bottom end of the second portion.

2. The Object of the Invention

The object of the instant invention is to militate to the fullest possible extent with the least amount of manufacturing expense against the possibility of loosening of an implanted artificial hip prosthesis and the invariably concomitant need for expensive and at least temporarily debilitating corrective surgery. The enhanced obviation of the potential need for such corrective surgery and in an relatively efficient economic manner, respectfully submitted, renders the instant invention unquestionably new, useful and unique.

A DESCRIPTION OF THE DRAWINGS

FIG. 16 illustrates a bored femoral shaft full of methyl methacrylate.

FIG. 17 illustrates a bored femoral shaft full of methyl methacrylate into which an artificial hip prosthesis has been introduced.

A DESCRIPTION OF THE PREFERRED EMBODIMENT

The instant applicator tube serves the purpose of maximizing the opportunity for greatly enhanced bone to cement bonding subsequent to the introduction of methyl methacrylate into a bored femoral shaft in anticipation of anchoring an artificial hip prosthesis during hip replacement surgery at a greatly reduced cost of manufacture as compared to other such devices of a comparable nature meant to serve a similar purpose.

Figure 1:
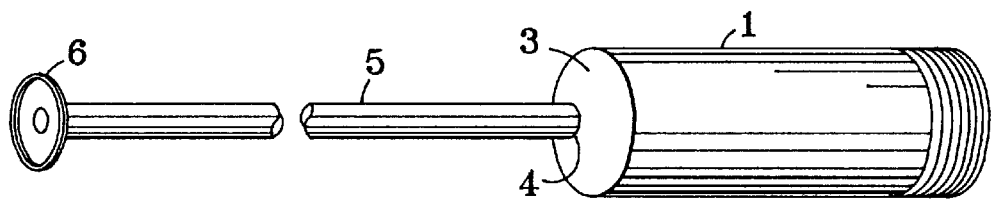
FIG. 1 is a perspective view of a first embodiment of the instant invention.
Figure 2:
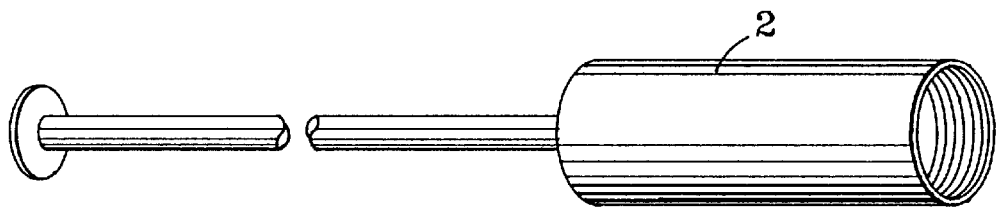
FIG. 2 is a perspective view of a second embodiment of the instant invention.
Figure 3:
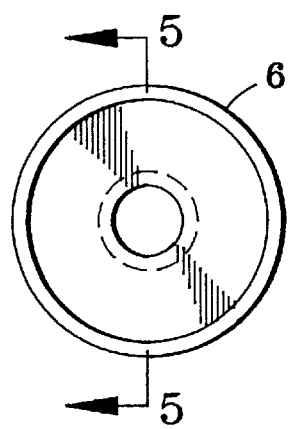
FIG. 3 is a bottom plan view of the circular shaped flexible tip component of the instant invention.
Figure 4:
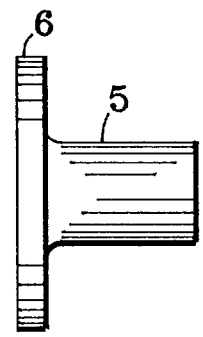
FIG. 4 is a lateral plan view of the circular shaped flexible tip component of the instant invention.
Figure 5:
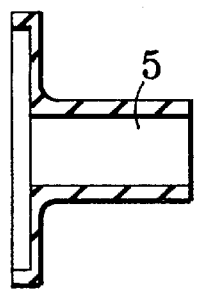
FIG. 5 is a lateral cross sectional view of the circular shaped flexible tip component of the instant invention.
Figure 6:
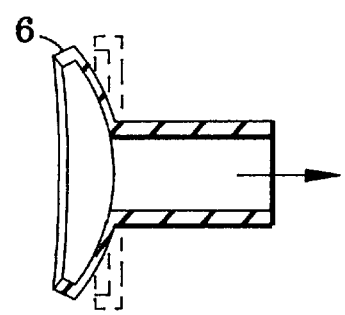
FIG. 6 is a later cross sectional view of the circular shaped flexible tip component of the instant invention illustrating distortion there of as the instant invention is withdrawn up a bored femoral shaft.
Figure 7:
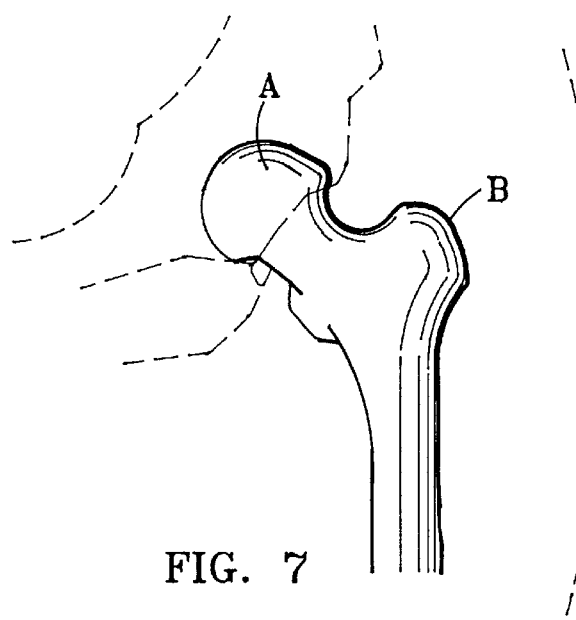
FIG. 7 is an isolated plan view of an intact human femoral bone just prior to the commencement of hip replacement surgery.
Figure 8:
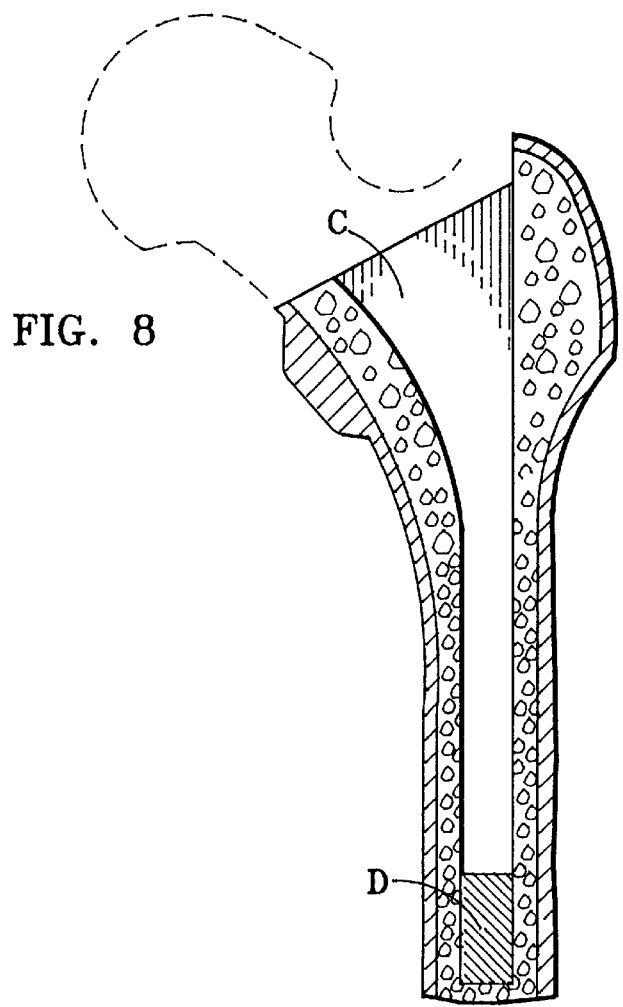
FIG. 8 is a cross sectional view of a human femoral bone with a shaft bored therein upon the commencement of hip replacement surgery subsequent to the removal of the acetabular head portion thereof seen in FIG. 7.
Figure 9:
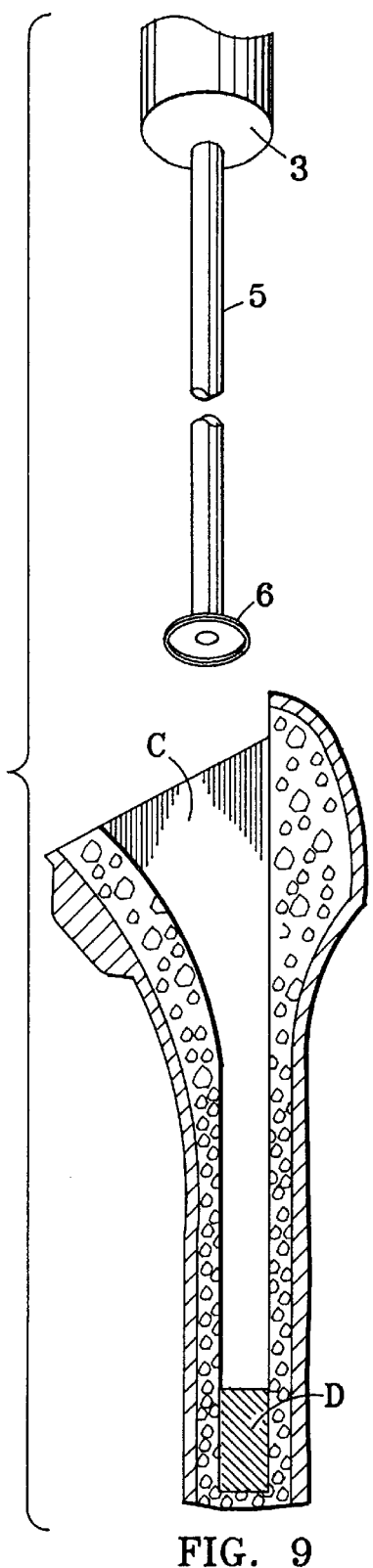
FIG. 9 is a plan view illustrating the manner of introduction of the instant invention into the bored femoral shaft shown in FIG. 8.
Figure 10:
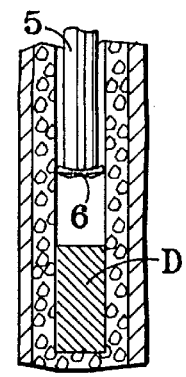
FIG. 10 illustrates the lowest part of the second portion of the instant invention near the very bottom of a bored femoral shaft.
Figure 11:
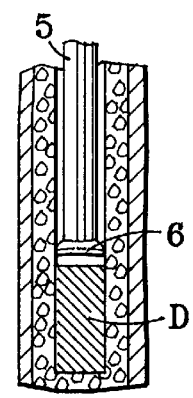
FIG. 11 illustrates the downward distortion of the circular shaped flexible tip component of the instant invention once withdrawal up a bored femoral shaft is initiated.
Figure 12:
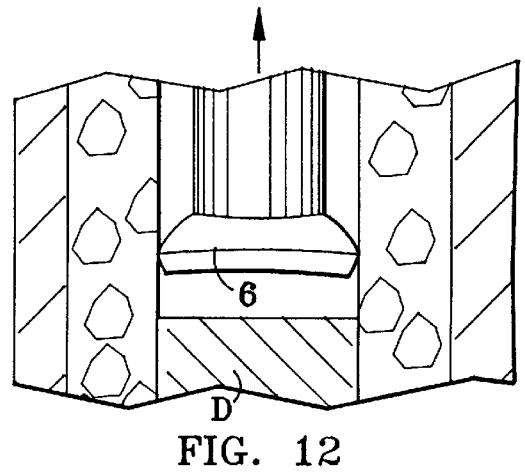
FIG. 12 is an amplified view of the region of FIG. 11 where such distortion is occurring.
Figure 13:
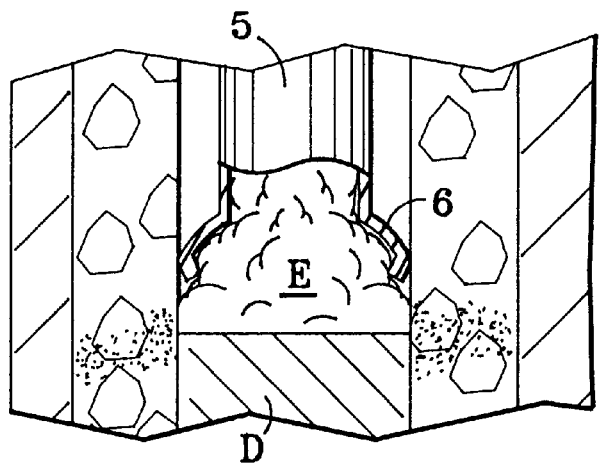
FIG. 13 illustrates the character of the closed space created within a bored femoral shaft by the circular shaped flexible tip component of the instant invention as methyl methacrylate is introduced therein.
Figure 14:
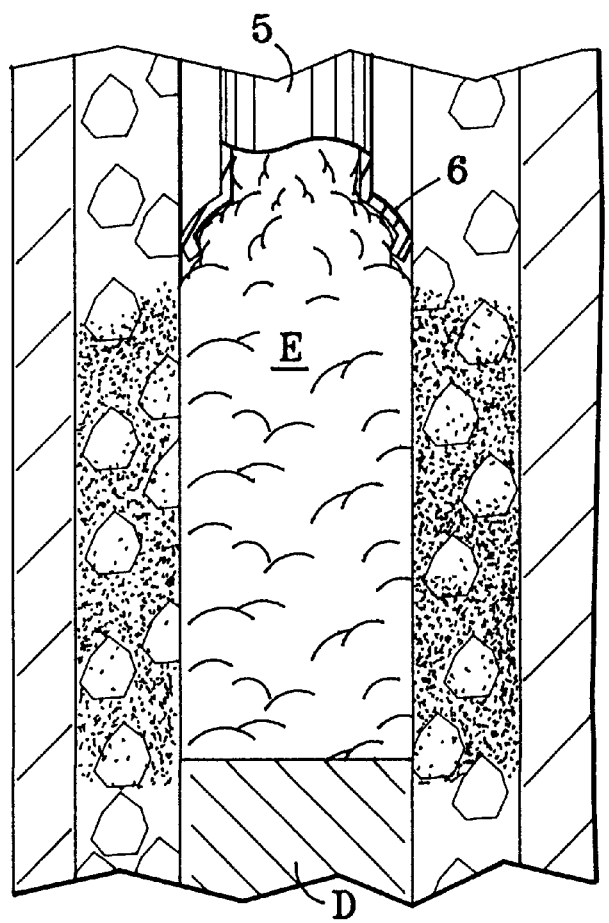
FIG. 14 illustrates the character of the closed space created within a bored femoral shaft by the circular shaped flexible tip component of the instant invention as methyl methacrylate is introduced therein after a succession of injections then withdrawals up the shaft.
Figure 15:
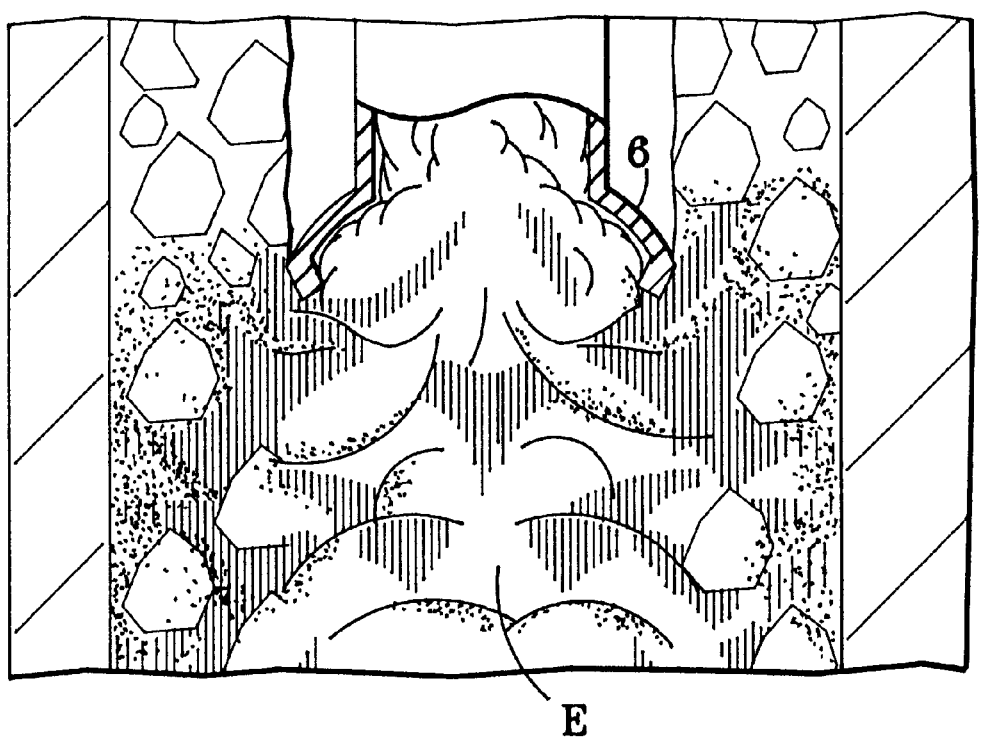
FIG. 15 illustrates pressure directed encroachment into bony interstitial spaces within the walling of the closed space depicted in FIG. 13.

FIGS. 1 and 2 are perspective views of the two embodiments of the instant invention. They differ from one another by virtue of the location of threading at the top end of a cylindrically shaped first portion 1 seen in FIG. 1 and a cylindrically shaped first portion 2 seen in FIG. 2. First portion 1 is hollow and is characterized by the presence of exterior threading about outer walling at and about a top end thereof serving to permit a ready attachment of first portion 1 to a methyl methacrylate holding syringe gun unit with threading about inner walling near a bottom end thereof. First portion 2 is also hollow and is characterized by the presence of interior threading about inner walling thereof at and about a top end thereof serving to permit a ready attachment of first portion 2 to a methyl methacrylate syringe gun unit with threading about outer walling near a bottom end thereof. FIG. 3 is a bottom plan view of a circular shaped flexible tip component 6 of the instant invention that is affixed to a bottom end of second portion 5 of the instant invention as shown in FIGS. 1 and 2. First portion 1 or first portion 2 as noted above are completely hollow cylindrically shaped units with diameters well in excess of the diameter of second portion 5 which is also completely hollow and cylindrically shaped. Second portion 5 is affixed at a top end thereof at a base 3 at a bottom end of portion 1 or portion 2 about a through hole 4 centrally located in base 3 as illustrated in FIGS. 1 and 2. FIG. 4 is a lateral plan view of component 6 affixed to a bottom end of second portion 5. FIG. 5 is a cross sectional view of what is seen in FIG. 4. FIG. 6 is a cross sectional view of what is seen in FIG. 4 and further serves to illustrate the manner in which component 6 affixed to and about a bottom end of second portion 5 distorts downwardly as the instant application tube is withdrawn by a surgeon up a previously bored femoral shaft C within the femoral bone B seen in FIG. 7 of a patient undergoing hip replacement surgery. FIG. 8 shows the bored femoral shaft within a femoral bone B of such a patient once the acetabular head component A thereof has been previously removed. FIG. 8 also shows a restrictor cap D which is placed by a surgeon at the base of femoral shaft C just prior to the advent of the process of introducing methyl methacrylate cement E as seen in FIG. 13 into the shaft C. FIG. 9 illustrates the concomitance of the instant invention to a bored shaft C. FIGS. 10 and 11 show the instant invention being placed into shaft C. FIG. 12 is a close up view of the instant invention upon its withdrawal up shaft C somewhat by a surgeon just prior to the introduction of methyl methacrylate bonding cement E into the subspace in shaft C as between restrictor cap D and flexible tip component 6. The subspace is an airtight closed subspace within shaft C by virtue of the above-mentioned downward distortion of component 6 upon withdrawal of the instant device upwards by a surgeon such that when methyl methacrylate E is then introduced therein, it not only fills the subspace but also oozes under pressure into the interstitial spaces within the bony walling of shaft C as depicted by peripherally drawn stopping as evidenced in FIG. 13, then FIGS. 14–17 thereby greatly enhancing bone to cement bonding upon hardening of such methyl methacrylate E all as can be better appreciated with resort to FIG. 15. Once the process depicted in FIGS. 12, 13, 14 and 15 is repeated during successive injections, new subspace creation and oozing of methyl methacrylate E into the interstitial spaces within the bony walling of shaft C all the way up shaft C as per FIG. 16 and the top layer of methyl methacrylate is tamped down tightly with a spongy tarp by the attending surgeon, an artificial hip prosthesis F is inserted into the methyl methacrylate filled shaft C as per FIG. 17 foreordained to be held tightly with a greatly minimized propensity for loosening due to perhaps an otherwise separation over time of hardened methyl methacrylate E from the waling of shaft C by virtue of the plethora of bone to cement, cement to cement bonding footings in the walling all the way up shaft C created in light of the surgeon's utilization of the instant new and unique applicator tube as noted above.

In closing, respectfully submitted, by virtue of the fact of the foregoing coupled with the relative economy of manufacture of the instant applicator tube, it is not only new and unique but unquestionably also highly useful.

What is claimed is:

1. A Biomedical Cement Bonding Enhancement Tube, comprising:
   a. a hollow cylindrically shaped first portion;
   b. threading about outer walling of said hollow cylindrically shaped first portion at a top end thereof;
   c. a base of said hollow cylindrically shaped first portion at a bottom end thereof;
   d. a through hole centrally located within said base;
   e. a hollow cylindrically shaped second portion affixed at a top end thereof to said base about said through hole;
   f. said hollow cylindrically shaped second portion having a diameter less than a diameter of said hollow cylindrically shaped first portion, and;
   g. a circular shaped flexible tip component affixed to and about a bottom end of said hollow cylindrically shaped second portion.

2. A Biomedical Cement Bonding Enhancement Tube, comprising:
   a. a hollow cylindrically shaped first portion;
   b. threading about inner walling of said hollow cylindrically shaped first portion at a top end thereof;
   c. a base of said hollow cylindrically shaped first portion at a bottom end thereof;
   d. a through hole centrally located within said base;
   e. a hollow cylindrically shaped second portion affixed at a top end thereof to said base about said through hole;
   f. said hollow cylindrically shaped second portion having a diameter less than a diameter of said hollow cylindrically shaped first portion, and;
   g. a circular shaped flexible tip component affixed to and about a bottom end of said hollow cylindrically shaped second portion.

* * * * *